(12) United States Patent
Ramadan et al.

(10) Patent No.: US 6,517,580 B1
(45) Date of Patent: Feb. 11, 2003

(54) DISK PROSTHESIS FOR CERVICAL VERTEBRAE

(75) Inventors: Aymen Ramadan, Carouge (CA); Markus Bühler, Uster (CH)

(73) Assignee: Scient'x Societe a Responsabilite Limited, Paris (FR)

( * ) Notice: Subject to any disclaimer, the term of this patent is extended or adjusted under 35 U.S.C. 154(b) by 0 days.

(21) Appl. No.: 09/521,896

(22) Filed: Mar. 9, 2000

(30) Foreign Application Priority Data

Mar. 3, 2000 (FR) .............................. 00 02791

(51) Int. Cl.[7] .................................................. A61F 2/44
(52) U.S. Cl. .................................. 623/17.15; 623/17.14
(58) Field of Search ........................... 623/17.11, 17.14, 623/17.15, 17.16

(56) References Cited

U.S. PATENT DOCUMENTS

| | | | | |
|---|---|---|---|---|
| 5,314,477 A | * | 5/1994 | Marnay | 623/17.11 |
| 5,401,269 A | * | 3/1995 | Buttner-Janz et al. | 623/17.15 |
| 5,676,701 A | * | 10/1997 | Yuan et al. | 623/17.15 |
| 5,899,941 A | * | 5/1999 | Nishijima et al. | 623/17.15 |
| 6,019,792 A | * | 2/2000 | Cauthen | 623/17.15 |
| 6,146,421 A | * | 11/2000 | Gordon et al. | 623/17.15 |
| 6,179,874 B1 | * | 1/2001 | Cauthen | 623/17.14 |

FOREIGN PATENT DOCUMENTS

| | | |
|---|---|---|
| EP | 0 699 426 | 3/1996 |
| FR | 2 694 882 | 2/1994 |

* cited by examiner

*Primary Examiner*—David H. Willse
*Assistant Examiner*—Suzette J. Jackson
(74) *Attorney, Agent, or Firm*—Bacon & Thomas, PLLC

(57) ABSTRACT

A disk prosthesis for cervical vertebrae. The prosthesis includes a spherical cap formed on a first insert, while a spherical cup is formed on a second inset, two inserts made of ceramic material, one of the inserts being mounted on a first plate while the other insert is mounted on a second plate in such a manner that the center of rotation of the joint is substantially centered relative to the edges of the plates, a spherical cup possessing a contact surface area that is not less than that of the spherical cap and being connected via an annular molding to the base of the insert, and a plate provided with the insert having the spherical cap includes an annular setback to leave clearance for the annular molding.

14 Claims, 1 Drawing Sheet

DISK PROSTHESIS FOR CERVICAL VERTEBRAE

The invention relates to a disk prosthesis for cervical vertebrae, intended to replace the fiber and cartilage disk that interconnects cervical vertebrae in the spinal column.

BACKGROUND OF THE INVENTION

It is known that an intervertebral disk can be subject to damage, such as compression, deformation, displacement, or wear, and more generally degeneration associated with the mechanical stresses that are applied thereto and that lead to anatomical and functional destruction of the disk and of the vertebral segment. This damage to the disk alters its mechanical behavior and leads to a reduction in the height of the intersomatic gap, which leads to all of the functions of the joint being disturbed. This gives rise to instability which induces, in particular, an osteoarthritic reaction which is painful and gives rise to osteophytic processes.

Proposals have therefore been made to replace the defective disk with an artificial disk, and various types of embodiment have been envisaged. Thus, a disk prosthesis is known, e.g. from patent FR 2 718 635, for cervical vertebrae where the prosthesis comprises first and second plates for fixing to adjacent cervical vertebrae. That prosthesis also has a ball joint interposed between the two plates that are mounted in a superposed position. The joint comprises a spherical cap made of a synthetic material, such as polyethylene, mounted on one of the plates and designed to co-operate with a spherical cup provided in the other plate and made of a metal, such as titanium, for example.

Although such a cervical prosthesis makes it possible to restore an appropriate height to the intersomatic gap, the ball joint of that prosthesis is subject to high levels of friction, making it sensitive to wear, and as a consequence of the wear that prosthesis does not give full satisfaction firstly because of its relative instability, particularly in bending movements.

A disk prosthesis for lumbar vertebrae is also known, in particular from patent U.S. Pat. No. 5,562,738, which comprises first and second plates for fixing to adjacent vertebrae, and made of a metal, such as titanium. Between the plates, a ball joint is interposed that comprises a first insert mounted on one of the plates and constituted by a spherical cap co-operating with a spherical cup of a second insert mounted on the other plate. The inserts are made of a biocompatible ceramic material having improved tribological characteristics, in particular concerning resistance to wear.

Nevertheless, such a disk prosthesis for lumbar vertebrae is unsuitable for replacing the disk of cervical vertebrae insofar as such a prosthesis does not enable cervical vertebrae to recover their natural mobility. It also turns out that the ball joint presents a shape that is quite difficult to get right and that is sensitive to breaking or cracking phenomena that reduce the lifetime of the prosthesis.

OBJECT AND SUMMARY OF THE INVENTION

The object of the present invention is thus to remedy the drawbacks of the state of the art by proposing a disk prosthesis for cervical vertebrae that is designed to present relative long lifetime by being practically insensitive to phenomena of wear and breaking, and while being suitable for providing physiological mobility between the two cervical vertebrae to which it is fitted.

To achieve this object, the prosthesis of the invention is of the type comprising:

first and second plates designed to be fixed to adjacent cervical vertebrae; and a ball joint interposed between the two plates mounted in a superposed position, the joint being constituted by a spherical cap co-operating with a spherical cup.

According to the invention:

the spherical cap is provided on a first insert, while the spherical cup is provided on a second insert;

each insert is made of a ceramic material and possesses a base of circular right cross-section;

one of the inserts is mounted on the first plate while the other insert is mounted on the second plate in such a manner that the center of rotation of the joint lies substantially centered relative to the edges of the plates so as to be centered in the sagittal plane and in the frontal plane of the vertebrae;

the spherical cup possesses a contact area that is not less than the contact area of the spherical cap and is connected via an annular molding to the base of the insert; and the plate provided with the insert having the spherical cap has an annular setback to leave clearance for the annular molding of the spherical cup during movements of the plates.

BRIEF DESCRIPTION OF THE DRAWING

Various other characteristics appear from the following description given with reference to the accompanying drawing which shows, as non-limiting examples, implementations and embodiments of the invention.

MORE DETAILED DESCRIPTION

Figure 1:
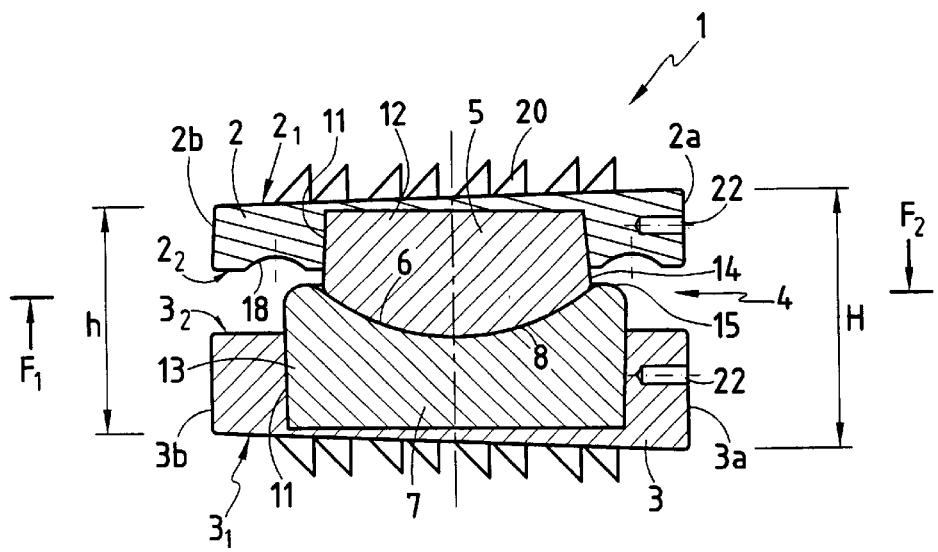
FIG. 1 is a section in elevation of a first embodiment of a prosthesis in accordance with the invention.
Figure 2:
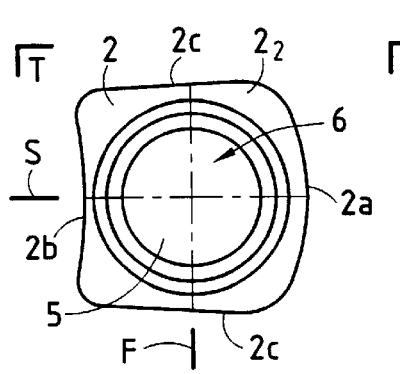
FIG. 2 is an inside view as seen substantially along arrow $F_1$, showing a first plate forming a portion of the prosthesis of the invention.
Figure 3:
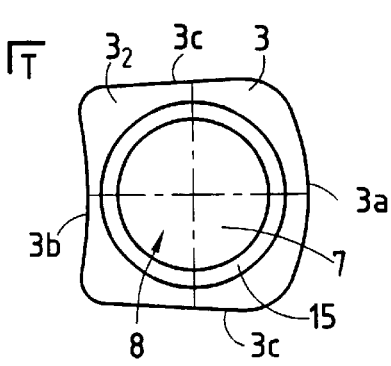
FIG. 3 is an inside view as seen substantially along arrow $F_2$, showing a second plate forming a portion of the prosthesis of the invention.

As can be seen more clearly in FIGS. 1 to 4, the subject matter of the invention is a disk prosthesis 1 for implanting as a replacement for a disk between two adjacent cervical vertebrae. The cervical prosthesis 1 of the invention comprises a first plate 2, referred to as a top plate in the example shown, and a second plate 3 referred to as a bottom plate. The plates 2 and 3 are designed to be fixed to adjacent cervical vertebrae and each has a respective outer face $2_1$, $3_1$ of dimensions that are substantially similar and adapted to fit approximately to the outlines of the surfaces of the associated joint. Each plate 2 and 3 also has a respective inner face $2_2$ and $3_2$ that extends to face the other interface. The general shape of each of the plates 2 and 3 is that of a rectangular parallelepiped processing a respective posterior edge 2a, 3a extending at a distance from a respective anterior edge 2b, 3b. The anterior edge 2b, 3b of each plate 2, 3 is connected to the corresponding posterior edge 2a, 3a via two side edges 2c, 3c that are opposite each other. The edges 2a, 2b, 2c, and 3a, 3b, 3c are preferably straight in profile and they are interconnected by rounded corners. The posterior edge 2a, 3a of each plate preferably presents a profile that is convex in a transverse plane T, while the anterior edge 2b, 3b presents a profile that is concave.

The cervical prosthesis 1 of the invention also has a ball joint 4 interposed between the two plates 2 and 3 which are mounted in the superposed configuration. The ball joint 4 is constituted by a first insert 5 presenting a spherical cap 6 and by a second insert 7 presenting a spherical cup 8 that co-operates with the spherical cap 6. Each insert 5, 7 is designed to be mounted in a housing 11, preferably a blind housing (which refers to a bore with an end which is closed, as shown in FIG. 1), formed from the inside face $2_2$, $3_2$ of each plate 2 and 3. Each insert 5, 7 is generally circularly symmetrical in shape and possesses a respective base 12, 13 of circular right cross-section, with one of its ends being shaped to present the spherical cap 6 or the spherical cup 8. The right cross-section of the base 12, 13 of each insert 5, 7 is constant, or preferably tapering from the spherical cap 6 or the spherical cup 8. In this preferred embodiment, each reception housing 11 is complementary in shape to the insert 5, 7 so as to enable the inserts 5, 7 to be assembled conically in the plates 2, 3. Naturally, any other type of assembly could be envisaged for the inserts, e.g. by means of adhesive or by means of crimping. In an embodiment, provision might be made to fit a damping element against the end of the blind housing 11 so as to be interposed between the corresponding insert and the plate in order to camp the axial forces acting on the prosthesis.

In a preferred embodiment, the insert 5 provided with the spherical cap 6 is mounted on the top plate 2, while the insert 7 provided with the spherical cup 8 is mounted on the bottom plate 3. This disposition enables the ball joint 4 to absorb the forces to which it is subjected better.

The spherical cap 6 is defined by a contact surface having a radius of curvature that is equal to the radius of curvature of the contact surface that defines the spherical cup 8 so as to form a ball joint. The spherical cap 6 is connected to the base 12 of the first insert 5 via a connecting curve 14 while the spherical cup 8 is connected to the base 13 of the second insert 7 via a connecting curve forming an annular molding 15. In accordance with an advantageous characteristic of the invention, the spherical cup 8 possesses a contact surface area that is not less than that of the spherical cap 6 so as to obtain good mechanical behavior between the spherical cap 6 and the spherical cup 8. In other words, the base 13 of the second insert 7 provided with the spherical cup 8 has a circular right cross-section that is greater in area than the right cross-section of the base 12 of the first insert 5 that is provided with the spherical cap 6, because of the presence of the annular molding 15.

In accordance with another advantageous characteristic of the invention, the plate 2 provided with the first insert 5 presenting the spherical cap 6 has an annular setback 18 surrounding the housing 11 so as to provide clearance for the annular molding 15 of the spherical cup 5 during movements of the plates 2, 3. Naturally, the first insert 5 is mounted on the plate 2 in such a manner as to project from the inner face $2_2$ so as to enable it to co-operate with the spherical cup 8. Similarly, the second insert 7 is mounted so as to project relative to the inner face $3_2$ of the plate so as to obtain sufficient angular clearance between the plates without them coming into contact with each other.

In accordance with an advantageous characteristic of the invention, the inserts 5, 7 are made of a ceramic material. The inserts 5 and 7 are preferably made of ceramic materials of different hardnesses. For example, the second insert 7 provided with the spherical cup 8 can be made of zirconium oxide ($ZrO_2$) while the first insert 5 provided with the spherical cap 6 is made of aluminum oxide ($Al_2O_3$).

In accordance with another advantageous characteristic of the invention, the inserts 5, 7 are mounted on the plates 2 and 3 in such a manner that the center of rotation of the joint 4 is substantially centered relative firstly to the side edges 2c and 3c of the plates so as to be centered in the sagittal or antero-posterior plane S, and secondly relative to the anterior and posterior edges 2a, 3a; 2b, 3b of the plates so as to be centered in the frontal plane F of the vertebrae. Such a centered disposition for the center of rotation of the joint 4 enables the prosthesis 1 to reproduce the natural movements of the intervertebral disk of the cervical vertebrae.

By appropriate dimensioning of the joint 4 and of the position of its center of rotation, as defined above, the forces applied to the surfaces that are in contact are limited. It should be observed that the surfaces in contact corresponding to the spherical cap 6 and to the spherical cup 8 allow angular displacement equal to or less than 10°, such that rubbing always occurs between the inserts 5, 7, i.e. between surfaces that are made of ceramic material. This reduces the wear on the inserts. Amplitude of movement is limited by causing the plates 2, 3 to come into contact with each other. The engagement of the spherical cap 6 in the spherical cup 8 makes it possible to obtain stability for the joint 4 while providing it with suitable three-dimensional mobility that is practically identical to that provided by a natural disk.

The plates 2, 3 can advantageously be made of titanium and the contact surfaces with the vertebral plates of the vertebrae, i.e. the outer faces $2_1$, $3_1$ are preferably covered in hydroxy apatite or in surface effect titanium, for example, so as to improve anchoring between the prosthesis and the adjacent bone.

Figure 5:
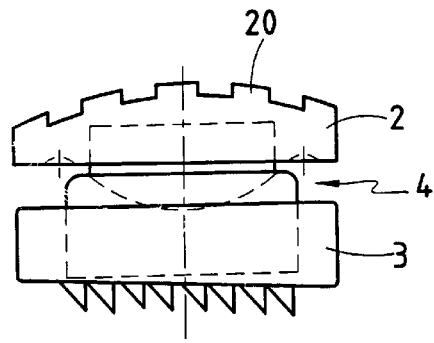
FIG. 5 is an elevation view of a second embodiment of a prosthesis of the invention.
Figure 6:
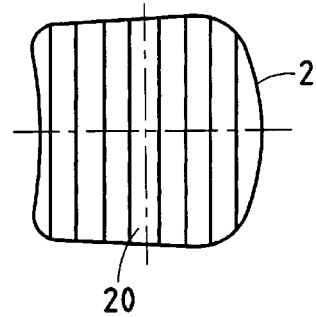
FIG. 6 is a plan view of the prosthesis shown in FIG. 5.

It should be observed that plates 2, 3 can be provided that are of different shapes adapted to possible different morphotypes of vertebral body. Thus, provision can be made for one or both of the plates 2, 3 to present different heights so as to enable them to match the height of the intersomatic gap that is to be reestablished. Furthermore, as shown in the example of FIG. 1, provision can be made for the outer faces $2_1$, $3_1$ of the plates 2 and 3 to present a plane profile optionally fitted with anchor elements 20 for anchoring in the vertebrae. In the example shown in FIGS. 1 and 4, each outer face $2_1$, $3_1$ possesses anchoring notches 20. In the example shown in FIGS. 5, 6, the outer face $2_1$ of the first plate 2 has notches as anchoring elements 20 that are parallel to one another and to the front plane F. It could be envisaged that the top plate 2 has a profile that is convex in the sagittal plane, as shown in FIG. 5. In accordance with another characteristic of the invention, at least one of the outer faces $2_1$, $3_1$ of the plates 2, 3 is provided with two anchoring studs (not shown) that are long enough to pass through each of the plates of the vertebrae so as to prevent the cage from sliding.

Figure 4:
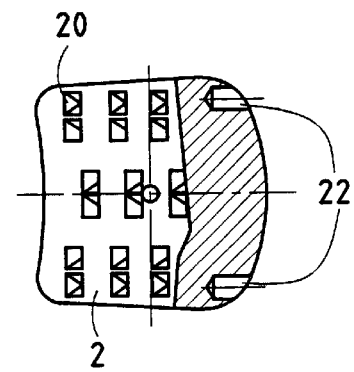
FIG. 4 is a plan view with the FIG. 1 prosthesis shown partially in section.

As can be seen more clearly in FIGS. 1 and 4, each plate 2, 3 is provided on its posterior edges 2a, 3a with two positioning holes 22 for the endpieces of a tool that serves to hold both plates simultaneously. It should be observed that in this position, as shown in FIG. 1, the plates 2, 3 form an angle in the sagittal plane S to facilitate insertion of the cage into the intersomatic gap. It can be seen that the height h of the prosthesis 1 at its front face as defined by the anterior edges 2b, 3b is smaller than its height H of its rear portion as defined by the posterior edges 2a, 3a. In accordance with a preferred characteristic the positioning holes 22 in any one plate converge on each other so as to facilitate withdrawal of the positioning tool.

The invention is not limited to the examples described and shown, since various modifications can be made thereto without going beyond its ambit.

What is claimed is:

1. A disk prosthesis for cervical vertebrae, the prosthesis being of the type comprising:

first and second plates designed to be fixed to adjacent cervical vertebrae; and a ball joint interposed between the two plates mounted in a superposed position, the joint being constituted by a spherical cap co-operating with a spherical cup, wherein:

the spherical cap is provided on a first insert, while the spherical cup is provided on a second insert;

each insert is made of a ceramic material and possesses a base of circular right cross-section;

one of the inserts is mounted on the first plate while the other insert is mounted on the second plate in such a manner that the center of rotation of the joint lies substantially centered relative to the edges of the plates so as to be centered in the sagittal plane and in the frontal plane of the vertebrae;

the spherical cup possesses a contact area that is not less than the contact area of the spherical cap and is connected via an annular molding to the base of the insert; and the plate provided with the insert having the spherical cap has an annular setback to leave clearance for the annular molding of the spherical cup during movements of the plates.

2. A disk prosthesis according to claim 1, wherein each plate is organized to present a blind housing for receiving an insert.

3. A disk prosthesis according to claim 1, wherein each plate is organized to present a blind housing for receiving an insert, and wherein each insert possesses a base whose circular right cross-section tapers from the spherical cap or the spherical cup, and matches the blind housing of complementary profile.

4. A disk prosthesis according to claim 1, wherein the inserts are made of ceramic materials of different hardnesses.

5. A disk prosthesis according to claim 4, wherein the insert fitted with the spherical cup is made of zirconium oxide, while the insert fitted with the spherical cap is made of aluminum oxide.

6. A disk prosthesis according to claim 2, including a damping element mounted in the end of the blind housing so as to be interposed between the insert and the plate.

7. A disk prosthesis according to claim 1, wherein the plate fitted with the spherical cap extends over the plate fitted with the spherical cup.

8. A disk prosthesis according to claim 1, wherein the plate extending over the other plate has a top outer face that presents a profile that is convex in the sagittal plane.

9. A disk prosthesis according to claim 1, wherein each plate possesses an outer face of profile that is plane.

10. A disk prosthesis according to claim 8, wherein the outer face of at least one of the plates is provided with anchoring notches for anchoring in the vertebrae.

11. A disk prosthesis according to claim 10, wherein the anchoring notches are constituted by ribs that are parallel to one another and parallel to the posterior edges of the plates.

12. A disk prosthesis according to claim 8, wherein the outer face of at least one of the plates is provided with two studs for preventing the cage from sliding.

13. A disk prosthesis according to claim 1, wherein each plate is provided on its posterior edges with two positioning holes for the studs of a tool for holding both plates simultaneously, which plates, when in this position, form an insertion cone in the sagittal plane.

14. A disk prosthesis according to claim 1, wherein each plate has an anterior edge of profile that is concave in the transverse plane.

* * * * *